US010668215B2

(12) United States Patent
Ward et al.

(10) Patent No.: US 10,668,215 B2
(45) Date of Patent: Jun. 2, 2020

(54) TIP CAP FOR AUTOMATIC SYRINGE FILLING APPARATUS

(71) Applicant: BAXTER CORPORATION ENGLEWOOD, Englewood, CO (US)

(72) Inventors: Brian William Ward, Littleton, CO (US); James McCrea, San Carlos, CA (US); Stephen Norman Donnigan, Highlands Ranch, CO (US); Gregory Walter Hall, Los Gatos, CA (US); Roy Sven Hovland, Denver, CO (US); James Robert Hutchison, III, Denver, CO (US); Steve K. Kele, San Jose, CA (US); Michael Dickson Olichney, Aurora, CO (US); Jeffery Jonathan Rau, Littleton, CO (US); Tammy Lynn Stultz, Westminster, CO (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 820 days.

(21) Appl. No.: 14/984,913

(22) Filed: Dec. 30, 2015

(65) Prior Publication Data

US 2017/0189618 A1 Jul. 6, 2017

(51) Int. Cl.
*A61M 5/178* (2006.01)
*A61M 5/31* (2006.01)
*B65G 11/02* (2006.01)

(52) U.S. Cl.
CPC ........ *A61M 5/1782* (2013.01); *A61M 5/3134* (2013.01); *B65G 11/023* (2013.01);
(Continued)

(58) Field of Classification Search
CPC .. A61M 2005/3104; A61M 2005/3114; A61M 2005/312; A61M 2005/3106;
(Continued)

(56) References Cited

U.S. PATENT DOCUMENTS 3,721,241 A 3/1973 Klohr et al.
3,987,930 A * 10/1976 Fuson .................. A61M 39/20
220/287

(Continued)

FOREIGN PATENT DOCUMENTS

JP 2006-515196 5/2006
JP 2014140588 A 8/2014
(Continued)

OTHER PUBLICATIONS

International Preliminary Report on Patentability for related International Application No. PCT/US2016/068235; reported dated Jul. 3, 2018; (11 pages).

(Continued)

*Primary Examiner* — Kevin C Sirmons
*Assistant Examiner* — Alexandra Lalonde
(74) *Attorney, Agent, or Firm* — K&L Gates LLP

(57) ABSTRACT

A syringe tip cap is provided for use with an automatic syringe loading apparatus. The cap includes a body having an exterior surface and an interior surface, and having a first end and an opposite second end. The first end is defined by at least one generally "V"-shaped ramp on each of two sides of the exterior surface.

18 Claims, 13 Drawing Sheets

(52) U.S. Cl.
CPC .............. *A61M 2005/3104* (2013.01); *A61M 2005/3114* (2013.01)

(58) Field of Classification Search
CPC .......... A61M 39/20; A61M 39/1011; A61M 39/162; A61M 39/165; A61M 5/1782; A61M 5/3202; A61M 5/5086; A61M 2039/1061; A61M 25/002; A61M 5/3213; A61M 2005/3109; A61M 2205/586; B65D 41/02; B65D 41/00; B65D 41/04; B65D 41/16; B65D 41/165; B65D 41/17; B65D 41/18; B65D 41/185; B65D 41/34; B65D 2251/02; B65D 2251/023; B65D 59/06; B65G 11/023
See application file for complete search history.

(56) References Cited

U.S. PATENT DOCUMENTS

| | | | |
|---|---|---|---|
| 4,202,334 A * | 5/1980 | Elson | A61M 5/31 215/247 |
| 4,230,112 A | 10/1980 | Smith | |
| 4,340,148 A * | 7/1982 | Beckham | A61M 1/3627 215/247 |
| 4,929,232 A | 5/1990 | Sweeney et al. | |
| 4,991,629 A * | 2/1991 | Ernesto | A61M 39/20 138/89 |
| 5,785,691 A | 7/1998 | Vetter et al. | |
| 5,807,345 A * | 9/1998 | Grabenkort | A61M 5/3134 215/211 |
| 5,884,457 A | 3/1999 | Ortiz et al. | |
| 6,027,482 A | 2/2000 | Imbert | |
| 6,196,998 B1 | 3/2001 | Jansen et al. | |
| 6,604,903 B2 | 8/2003 | Osborne et al. | |
| 7,007,443 B2 | 3/2006 | Liedtke et al. | |
| D530,009 S | 10/2006 | Lyman et al. | |
| D530,817 S | 10/2006 | Lyman et al. | |
| 7,392,638 B2 | 7/2008 | Baldwin et al. | |
| 7,631,475 B2 | 12/2009 | Baldwin et al. | |
| 7,644,562 B2 | 1/2010 | Sullivan et al. | |
| 8,728,414 B2 | 5/2014 | Beach et al. | |
| 2004/0116869 A1* | 6/2004 | Heinz | A61M 5/347 604/181 |
| 2004/0215148 A1* | 10/2004 | Hwang | A61M 5/3134 604/187 |
| 2005/0039417 A1 | 2/2005 | Liedtke et al. | |
| 2008/0015539 A1 | 1/2008 | Pieroni et al. | |
| 2010/0185178 A1 | 7/2010 | Sharp et al. | |
| 2011/0174647 A1* | 7/2011 | Shimazaki | A61M 5/3134 206/365 |
| 2012/0111368 A1 | 5/2012 | Rahimy et al. | |
| 2015/0374968 A1* | 12/2015 | Solomon | A61B 90/70 604/535 |
| 2016/0144118 A1* | 5/2016 | Solomon | A61M 39/162 206/370 |

FOREIGN PATENT DOCUMENTS

| | | |
|---|---|---|
| WO | 2006085176 A1 | 8/2006 |
| WO | 2015147018 A1 | 1/2015 |
| WO | 2015085031 A1 | 6/2015 |
| WO | 2015147018 A1 | 4/2017 |

OTHER PUBLICATIONS

Japanese Office Action for related Japanese Application No. 2018-533237; action dated May 30, 2019; (6 pages).
European Office Action for related European Application No. 16826568.4; action dated Oct. 9, 2019; (4 pages).
Japanese Office Action and English translation for Japanese Application No. 2018-533237; action dated Dec. 20, 2019; (5 pages).

* cited by examiner

TIP CAP FOR AUTOMATIC SYRINGE FILLING APPARATUS

RELATED APPLICATIONS

This application relates to and incorporates by reference the co-owned application Ser. No. 62/272,786 by Stultz et al. filed on Dec. 30, 2015 entitled SYRINGE POSITIONING APPARATUS AND METHOD. This application relates to and incorporates by reference the co-owned application Ser. No. 62/272,794 by Ward et al. filed on Dec. 30, 2015 entitled CAPACITIVE SINGLE PLATE BUBBLE DETECTOR. This application relates to and incorporates by reference the co-owned application Ser. No. 14/984,022 by Ward et al. filed on Dec. 30, 2015 entitled SOURCE FLUID INLET ASSEMBLY FOR AUTOMATED FILLING DEVICE. This application relates to and incorporates by reference the co-owned application Ser. No. 62/272,798 by Hutchison et al. filed on Dec. 30, 2015 entitled SYRINGE GRIPPING APPARATUS AND METHOD. This application relates to and incorporates by reference the co-owned application Ser. No. 14/984,285 by Stultz et al. filed on Dec. 30, 2015 entitled SYRINGE PLUNGER POSITION APPARATUS AND METHOD.

BACKGROUND

The present invention relates generally to systems for filling or loading hypodermic syringes used in administering medicines, and in particular to a syringe cap for use in an automatic syringe filling apparatus.

In medical facilities such as hospitals, clinics, extended care centers and the like, it is typical to have a high volume use of syringes filled with a variety of solutions, including but not limited to saline and various medications that are commonly used for many patients (referred to here as "solutions"). The conventional practice is for the hospital pharmacist or technician to manually load or fill (the terms are used interchangeably in this application) each syringe to the designated volume of solution. Depending on the size of the syringe, loading a consistent amount of solution results in the syringe piston being retracted a different distance from one sized syringe to the next. This work is tedious, and prone to human error.

Thus, there is a need for an improved device that automatically fills syringes with a desired amount of solution and accommodates various sizes of syringe.

SUMMARY

The above-identified need is met by the present removable syringe tip cap, which is constructed and arranged for use with an automatic syringe filling apparatus. In general, the apparatus accepts syringes with caps either loaded manually onto the syringe outlet port (typically a needleless luer-style or the like) by a technician, or automatically loaded by a magazine attachment on the apparatus. The magazine apparatus accepts caps nested end-to-end in a stack and enclosed in tubular packages. Each cap-filled tube is loaded into the magazine. The apparatus accommodates multiple cap-filled tubes and automatically rotates them sequentially into position whereby, the next cap is stripped from the package and is guided down a feed track, to a syringe mounting point where the cap is attached to a tubular outlet such as a male luer fitting found on the syringe.

The syringe with attached tip cap may then be moved to an assembly to mount, exactly locate and align the syringe for further processing such as filling, labelling etc. The cap includes features that engage with the mounting assembly to provide for the location and alignment of the syringe for all common syringe sizes. At the syringe mounting point, a sensor is mechanically activated by a male end of the cap only when the syringe and cap are properly aligned for subsequent automatic filling.

Once the syringe is properly aligned and the cap secured, the apparatus is configured so that a decapping and loading fixture engages the syringe. Operationally, the decapping apparatus laterally reciprocates between a decapping position, in which the cap is temporarily removed from the syringe, and a filling position, in which a filling port is engaged with the syringe outlet, and the syringe piston is automatically retracted. During the latter step, a sensor system on the apparatus monitors the linear displacement of the piston relative to the syringe barrel in view of the syringe gradient, and regulates the piston movement so that the piston is retracted the proper amount to load the syringe with the designated amount of fluid. The automatic filling system bases many of the syringe handling functions on the position of the syringe and the cap at the syringe mounting point, so proper syringe and cap alignment are important to desired operation of the system.

After the syringe is filled to the designated amount, the syringe is disengaged from the filling port, the decapping fixture is then reciprocated back to the decapping position, and the cap is again aligned with the syringe luer fitting. The cap is replaced on the syringe, and the capped syringe is then transported to subsequent stations in the filling apparatus.

Accordingly, the present tip cap, which is mountable on any conventional syringe, includes features for engaging rails of the present apparatus, which store and transport the capped syringes to the syringe mounting, location and alignment assembly. Other features on the cap are configured for engaging the decapping portion of the decapping and loading fixture. Still other features are configured for properly engaging the syringe mounting point sensor so that the system automatically recognizes that the cap and attached syringe are properly mounted and aligned. The cap is also configured for matingly and nestingly engaging adjacent caps in a package, for use in embodiments when the caps are automatically provided in a magazine attachment for the apparatus. In addition, an outer diameter of the cap is constructed and arranged for engaging specialized flanged syringes.

In another embodiment, a modified version of the present tip cap is configured with a generally planar lower flange for slidingly engaging an upper surface of an elongate syringe storage/delivery rail having a generally rectangular cross-section with an upper, axially extending slot. This rail replaces the gravity feed track described above. The syringe and cap assemblies are slidably engaged on the rail. Once the syringes are ready for use, the rail and syringes are inverted and inclined so that the syringes slide by gravity towards the automatic decapping and filling apparatus. In the inverted position, the present cap slides along an inner surface of the rail along "V"-shaped ramps.

More specifically, a syringe tip ap is provided for use with a syringe loading apparatus. The cap includes a body having an exterior surface and an interior surface, and having a first end and an opposite second end. The first end includes at least one, generally "V"-shaped ramp on each of two sides of the exterior surface. In other words, the two sides of the exterior surface include and are partially defined by at least one, generally "V"-shaped ramp.

In another embodiment, a syringe tip cap is provided for use with an automatic syringe loading apparatus. The cap includes a body with an exterior surface and an interior surface, and having a first end portion and an opposite second end portion. The first end portion includes at least one generally "V"-shaped ramp on each of two outwardly facing sides of the exterior surface. In addition, the body has a pair of undercut shoulders when viewed in a second vertical cross-section taken transverse to the first vertical cross-section, and the interior surface is connected to an axially extending connector portion having a first, male end extending beyond an upper edge of the body and a second, female end.

In still another embodiment, a rail for use in a syringe loading apparatus, is provided, including an elongate body with a generally rectangular cross-section, and an upper surface with an axially extending slot, an inner wall with a second, axially extending slot vertically displaced from the axially extending slot in the upper surface, the second slot being narrower than the axially extending slot. A main chamber being defined between the upper surface and the inner wall, and a tip chamber being defined between the inner wall and a bottom wall of the rail.

DETAILED DESCRIPTION

Figure 1:
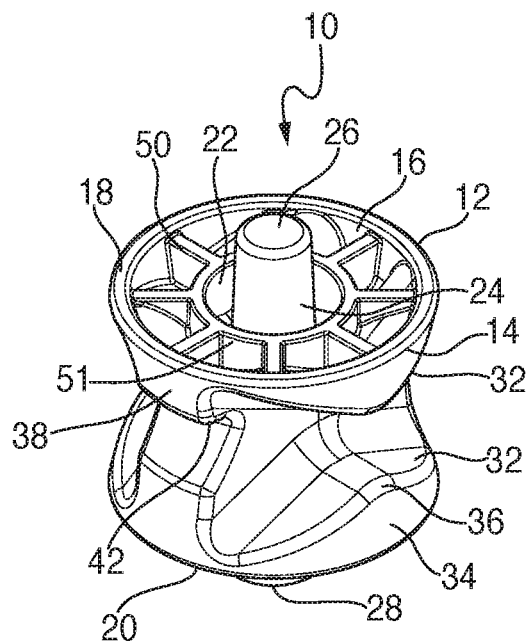
FIG. 1 is a top perspective view of the present tip cap.
Figure 2:
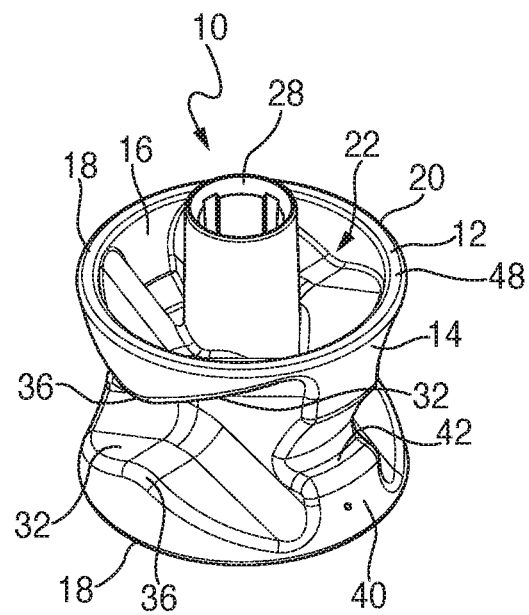
FIG. 2 is a bottom perspective view of the present cap taken from a different angle from the position of FIG. 1.

Referring to FIGS. 1-9, a syringe tip cap for use with an automatic syringe loading apparatus is generally designated 10. It is contemplated that the present cap 10 is useful in not only maintaining an outlet of the corresponding syringe in a sterile condition, but also facilitates the handling, orienting and loading of the syringe on the companion automatic syringe loading apparatus. The cap 10 is considered disposable, in that once the syringe is filled with the designated fluid, and the fluid is dispensed, the cap is intended to be disposed of.

Included on the cap 10 is a body 12, which in the preferred embodiment is generally tubular, having an exterior surface 14 an interior surface 16, a first or upper end or end portion 18 and a second or lower end or end portion 20, the "upper" and "lower" designations being arbitrary, and relating to the orientation of the cap 10 in FIGS. 1, 2 and 5-8. The interior surface 16 defines an interior chamber 22 in which is disposed an axially extending connector portion 24, constructed and arranged to be radially spaced from the interior surface. A first, male end or tip 26 is adjacent to, and extends beyond the upper end 18, and a second or female end 28 is adjacent to, and extends past the lower end 20. In the preferred embodiment, each of the male end 26 and the female end 28 extend axially past respective edges of the body 12 approximately the same distance, however other distances are contemplated depending on the application.

Figure 5:
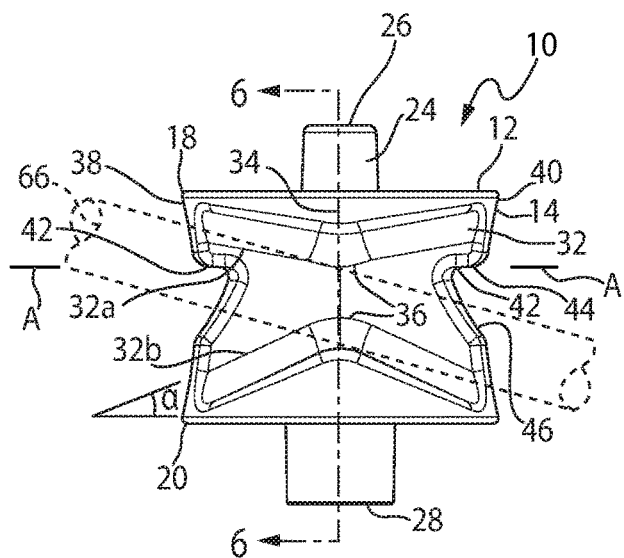
FIG. 5 is a side elevation of the present cap.
Figure 6:
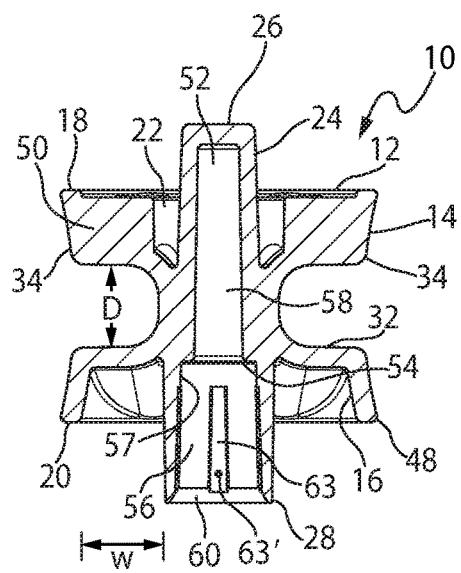
FIG. 6 is a cross-section, taken along the line 6-6 of FIG. 5 and in the direction generally indicated.
Figure 7:
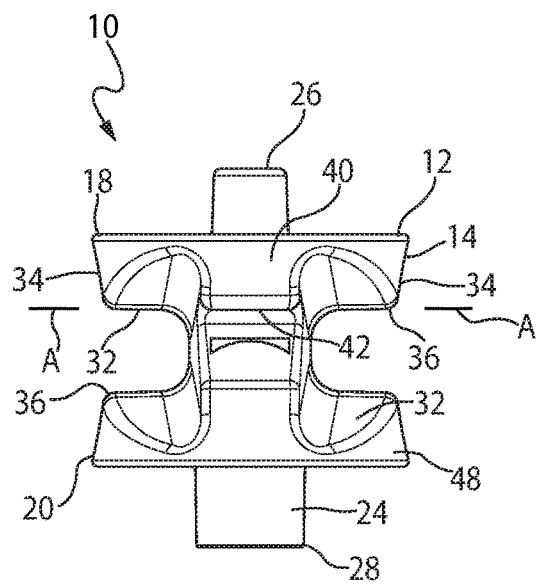
FIG. 7 is a side elevation of the present cap, having been rotated approximately 90 degrees from the position of FIG. 5.

Referring now to the exterior surface 14, the cap 10 is provided with specially designed formations for facilitating the engagement of the cap and a corresponding syringe, generally designated 30 (FIGS. 11, 13 and 14) with the automatic syringe loading apparatus referenced above. The structural features of the cap exterior surface 14 enhance the ability of the apparatus to accurately position, handle and orient the syringe 30. As seen in FIGS. 5-7, the cap 10 in this embodiment has a general hourglass shape when viewed in a first vertical cross-section and as also seen in an end view. This hourglass shape is defined in part by a pair of opposed, generally "V"-shaped ramps 32 on each of two sides 34 of the exterior surface 14. Referring to FIG. 5, the ramps 32, designated 32a and 32b, each have an apex 36 with a rounded point, the apexes of the opposing ramps point to each other and are the closest point of the corresponding ramps 32a, 32b on each side 34. In addition, the apexes 36 are spaced apart from each other a designated distance that is sufficient for slidingly accommodating rails of the apparatus, as will be described in more detail below. Referring also to FIG. 6, it will be seen that the respective "V"-shaped ramps 32 extend radially and have a width "W" which is approximately the same as a distance "D" between the apexes 36. Also as described below, it is contemplated that the cap 10 has at least one generally "V"-shaped ramp 32 on each of two sides 34 of the exterior surface 14f.

Figure 8:
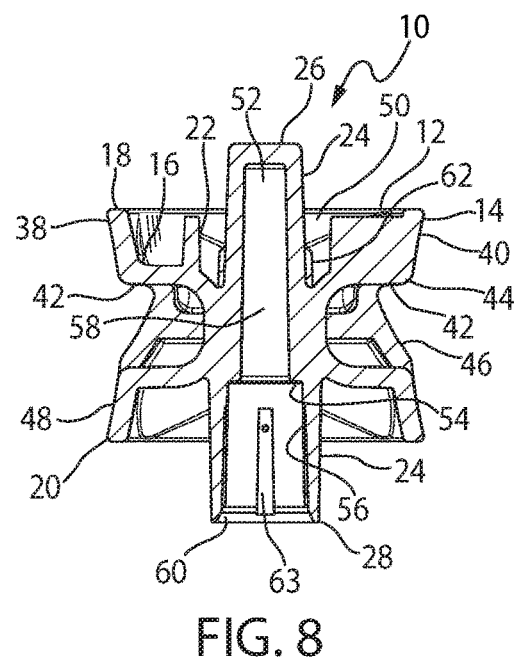
FIG. 8 is a cross-section taken along the line 8-8 of FIG. 7 and in the direction generally designated.

Referring now to FIGS. 5 and 8, front and rear ends 38, 40, referred to as such mainly to relate to the sides 34, the body 12 has a pair of undercut shoulders 42 when viewed in a second vertical cross-section of FIG. 7 taken transverse to the first vertical cross-section of FIG. 5. The shoulders 42 each have a generally horizontal portion 44 continuous with an inclined portion 46 sloping towards the lower end 20. As seen in FIGS. 5 and 7, the horizontal portion 44 is preferably aligned with the corresponding apex 36 of the "V"-shaped ramp 32a along a plane "A" extending transverse or perpendicular to a vertical axis of the body 12.

Figure 3:
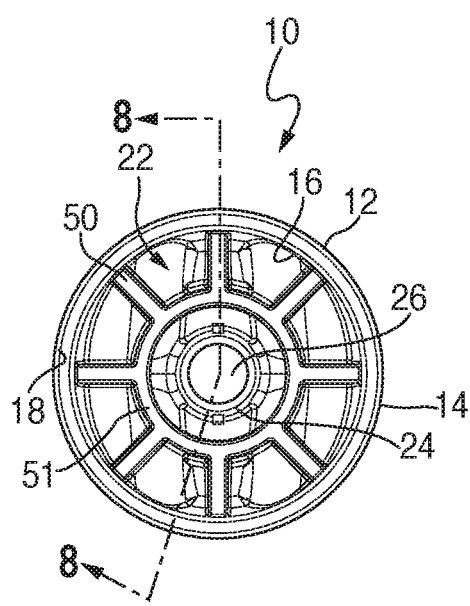
FIG. 3 is a top plan view of the present cap.
Figure 4:
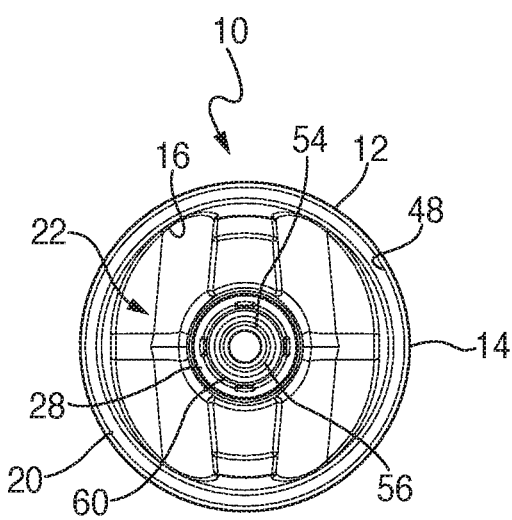
FIG. 4 is a bottom plan view of the present cap.

The sloping portion 46 extends around the periphery of the lower end 20 and defines a skirt 48 (best seen in FIGS. 6, 8). As seen in FIGS. 1 and 3, at the first end 18, opposite the skirt 48, the interior chamber 22 is supported by a plurality of support ribs 50 forming a radial array and connecting the interior surface 16 to a ring 51 circumscribing the axially extending connector portion 24. Support provided by the ribs 50 and the ring 51 allow for the use of more resilient plastic material in fabricating the cap 10. In an embodiment, the cap 10 may be made of a thermoplastic elastomer such as HYTREL TPE from Dupont. In addition, the ribs 50 are optionally usable in the capping/decapping process as splines for preventing rotation of the cap 10 in the apparatus.

Figure 10:
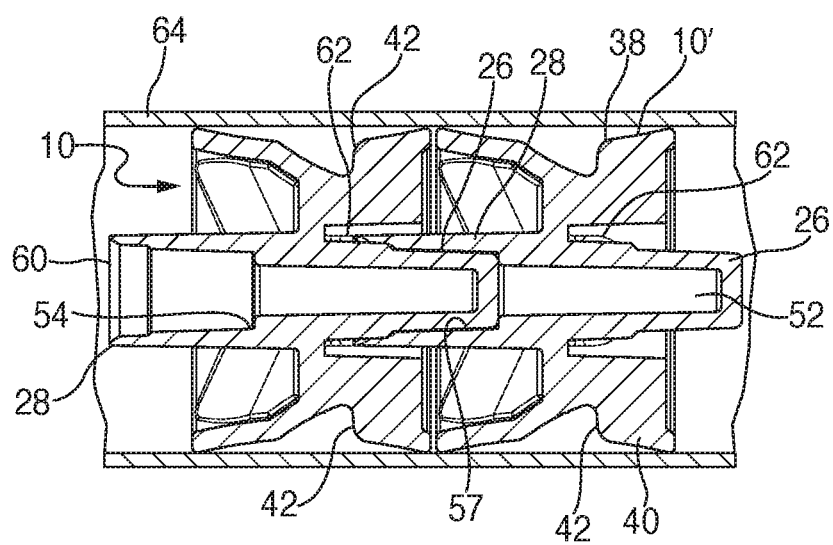
FIG. 10 is a cross-section of a pair of the present caps nested together in a package for use with a magazine feed in a syringe filling apparatus.
Figure 13:
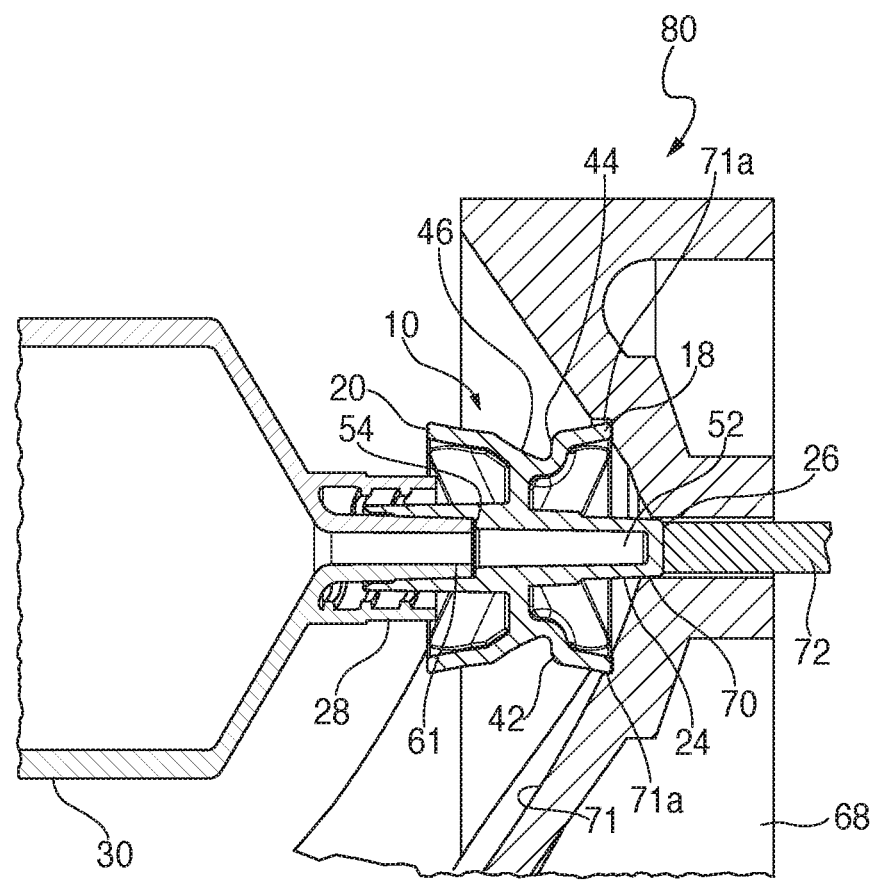
FIG. 13 is a fragmentary vertical cross-section of a syringe alignment funnel and a syringe equipped with the present cap being checked for proper cap alignment.
Figure 14:
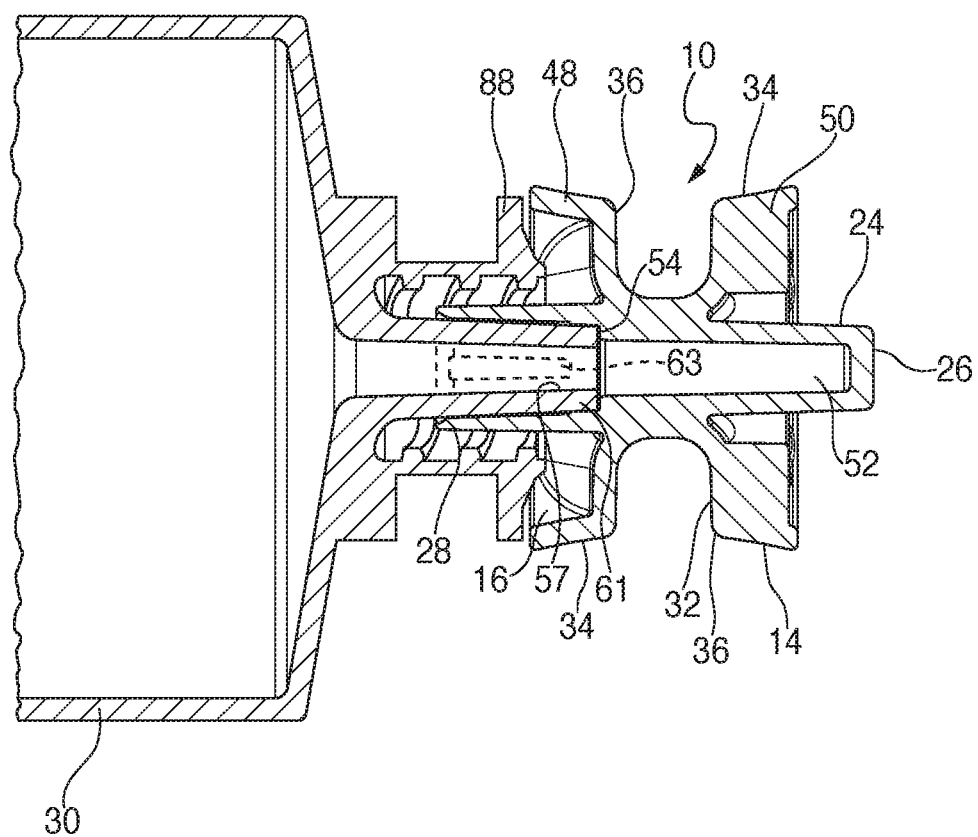
FIG. 14 is a vertical cross-section of the present cap mounted on a B-Braun PERFUSOR® syringe.
Figure 15:
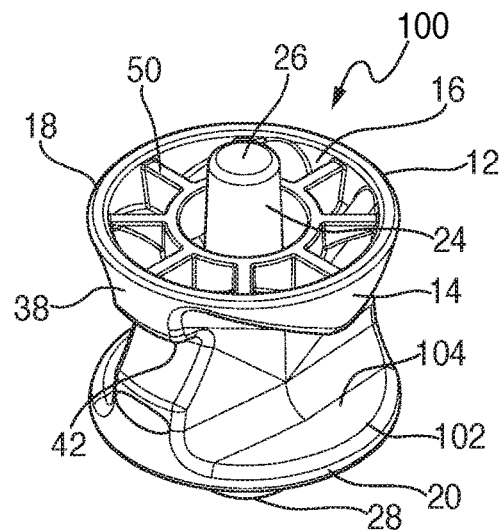
FIG. 15 is a top perspective view of an alternate embodiment of the present cap.
Figure 16:
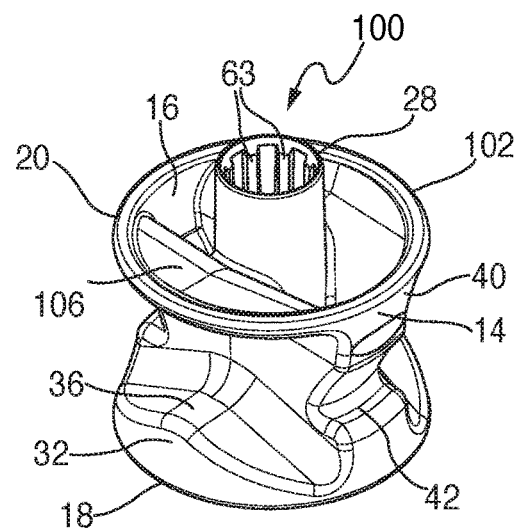
FIG. 16 is a bottom perspective view of the cap of FIG. 15 taken from a different angle from the position of FIG. 15.
Figure 17:
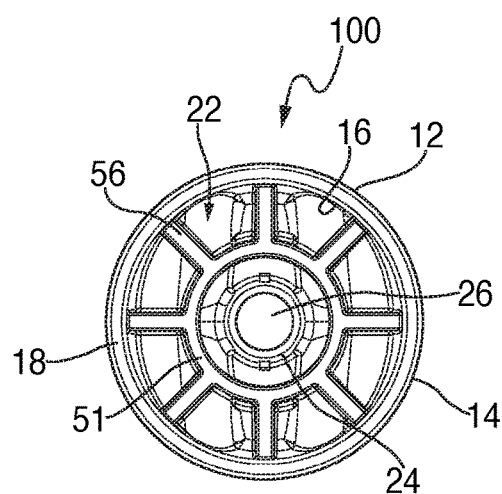
FIG. 17 is a top plan view of the cap of FIG. 15.
Figure 18:
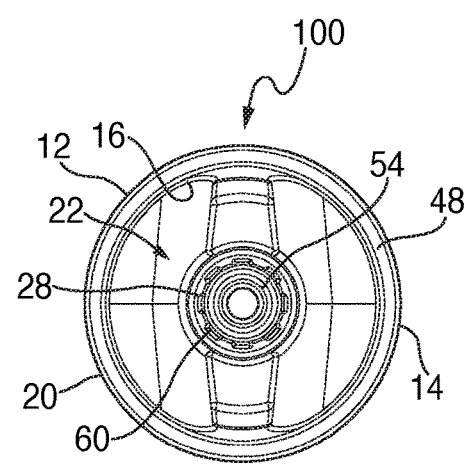
FIG. 18 is a bottom plan view of the cap of FIG. 15.
Figure 19:
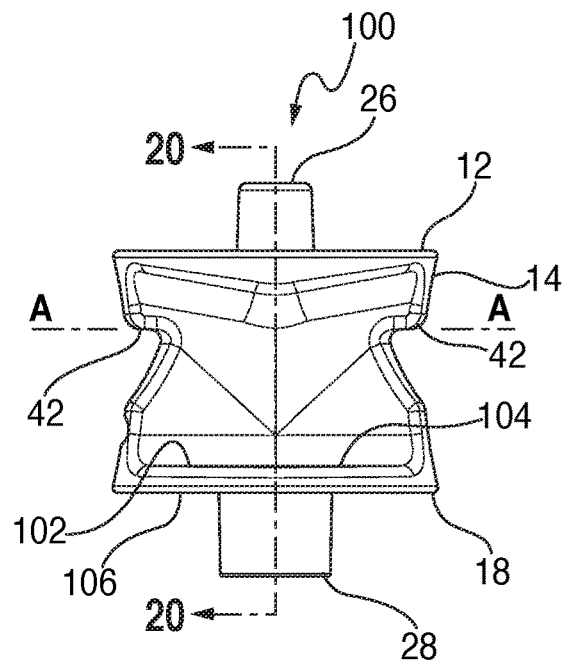
FIG. 19 is a side elevation of the cap of FIG. 15.
Figure 20:
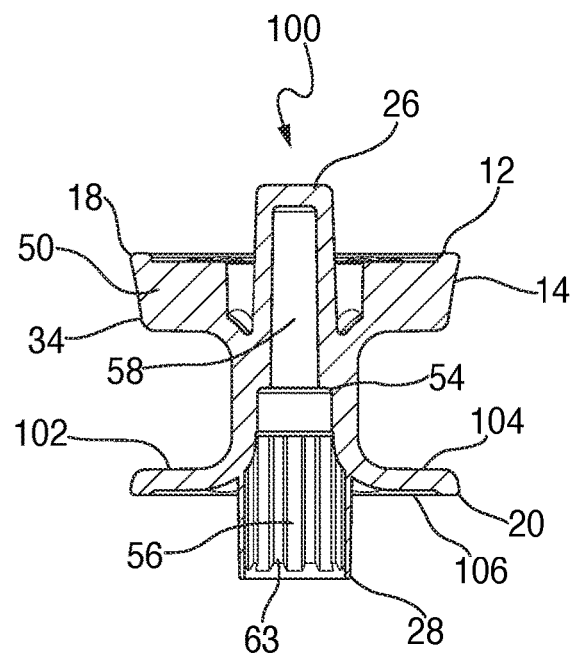
FIG. 20 is a cross-section taken along the line 20-20 of FIG. 19 in the direction generally indicated.

Referring again to FIGS. 6 and 8, the connector portion 24 has an interior chamber 52 divided by a landing or internal step 54 defining a sealing seat that separates a female portion 56 of the chamber, corresponding to the female end 28 from a male portion 58 corresponding to the male end 26. In the preferred embodiment, the female portion 56 has an interior sealing surface 57 that tapers towards the male end 26, and also has a diametrically flared end 60 dimensioned to receive a corresponding male end 26 of an adjacent cap 10 when multiple caps are nested together, as in a tubular package incorporated in a magazine of the apparatus (FIG. 10). Nesting of the caps 10 helps to maintain the sterility of the female portion 56. The step or landing 54 defines an end point for insertion of the male end 26. In addition, the female portion 56 of the second end 28 is configured for engaging an outlet or needle end 61 of a conventional syringe 30, more specifically an ISO-594-1 compatible luer taper, so that a sterile barrier is maintained once the cap 10 is mounted upon a syringe (FIGS. 13, 14). The landing 54 also defines an insertion end point for the syringe outlet end 61. The tapered configuration of the female chamber portion 56 is dimensioned to enhance locating of the syringe 30 and improving lead-in tolerances of the nested caps.

Figure 9:
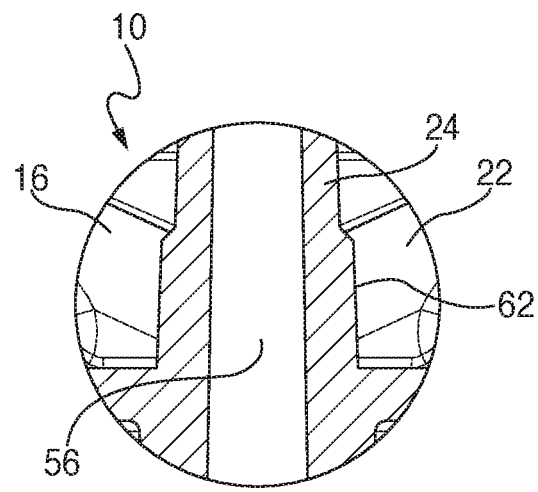
FIG. 9 is an enlarged fragmentary view of the cap of FIG. 8.

Referring now to FIGS. 6, 9 and 10, the nested engagement of the caps 10 is enhanced by at least one and preferably a plurality of circumferentially spaced crush ribs 62 dimensioned for positively engaging the female end 28 of an adjacent cap when multiple caps are nested together. The crush ribs 62 extend generally parallel to the connector portion 24 and are constructed and arranged to create a positive friction fit. Further, the crush ribs 62 do not interface with the seal surface 57 of the tapered female chamber portion 56 (FIG. 10). In addition, at least one, and preferably four venting channels 63 are located in the female chamber portion 56. These channels 63 are configured with small apertures 63' for reducing compressed air during both syringe insertion and cap reapplication, which in some cases, when the compressed air has not been provided with an escape passage, has been found to move the syringe plunger to a false "overfilled" position. Thus, the channels 63 and the apertures 63' permit the escape of air from the cap interior chamber 52 upon insertion of the syringe outlet end 61 into the female cap end 28.

Referring again to FIG. 10, multiple caps 10 are shown nested together and packaged in a sleeve 64, as when supplied to the apparatus for loading in a cap magazine. Note that the male end 26 of the left cap 10 is positively engaged in the female end 28 of the right hand cap 10'. The crush ribs 62 enhance the positive mating engagement. Once in the apparatus, a leading cap 10', is stripped from a stack of the nested caps in the sleeve 64. The stripped cap 10 travels down a set of rails and is ultimately applied to a syringe 30.

Figure 11:
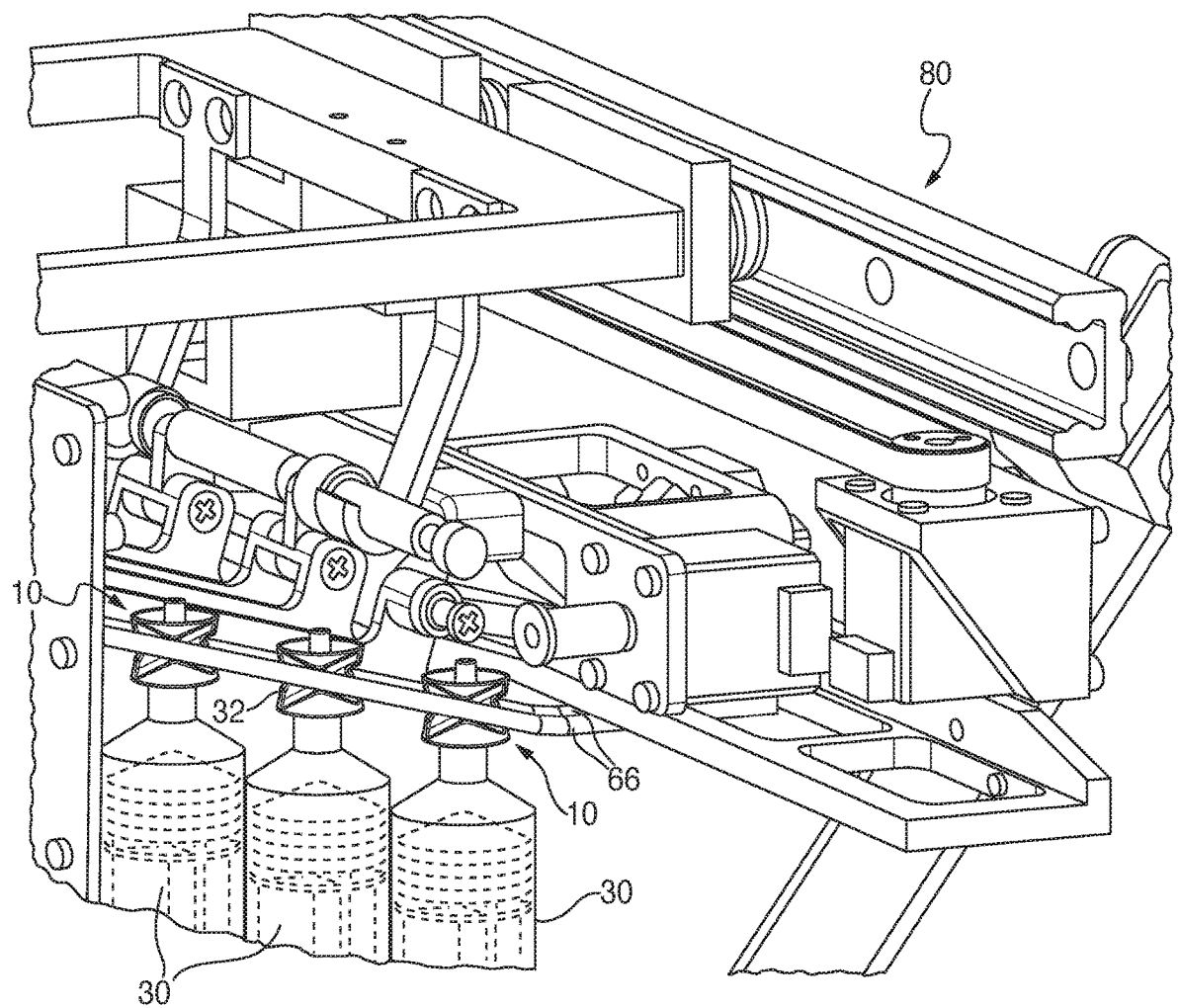
FIG. 11 is a fragmentary side perspective of a plurality of syringes equipped with the present cap and stored on rails of an automatic syringe filling apparatus.

Referring now to FIG. 11, multiple syringes 30, each equipped with a cap 10, are loaded in the apparatus. More specifically, the syringes 30 are slidingly engaged on spaced, inclined rails 66 by virtue of their engagement with the "V"-shaped ramps 32. It should be noted that an angle α defined by the "V"-shaped ramps 32 (FIG. 5) is configured to coincide with the angle of inclination of the rails 66 so that once suspended from the rails, the syringes 30 migrate towards a lower end of the rails and are stored in parallel, generally vertical orientation.

Referring now to FIG. 13, the syringe 30 and cap 10 are shown in an alignment cone 68 used for ensuring that the syringe is properly aligned in the apparatus. The cone 68 is configured so that the male end 26 of the cap 10 engages a syringe mounting point 70. Ultimately, the first end 18 circumferentially engages an annular seat 71a as the male end 26 is stabilized in its engagement with the syringe mounting point 70, which is located at an approximate apex of the surface 71.

In the preferred embodiment, the syringe mounting point 70 is a recess configured for matingly receiving the male end 26. Once the syringe 30 is properly aligned in the funnel 68 and the male end 26 is properly engaged in the syringe mounting point 70, with the first end 18 circumferentially engaged in the annular seat 71a, the male end 26 then is stabilized and properly extends into the mounting point a predetermined distance and depresses and thus engages and slightly moves a sensor rod 72. The movement of the sensor rod 72 activates a sensor 9, not shown, that confirms that the male end of the tip cap 10 and thereby the syringe 30 is properly positioned. This proper positioning is achieved through the engagement of the first end 18 in the seat 71a and the male end 26 matingly engaged in the syringe mounting point 70. Since the male end 26 is located a fixed distance from the syringe outlet end 61, the filling apparatus, generally designated 80, includes software for monitoring the position of the syringe 30 so that it can be accurately and automatically handled, decapped, filled and recapped. The software uses the position of the male end 26 engaging the sensor 72 to calculate the position of the syringe outlet 61. Thus, the relative axial extension distance of the male end 26 from the upper end 18, which engages the corresponding seat 71a of the funnel 68, is important for triggering the sensor 72 and for providing information to the automatic filling apparatus, generally designated 80. The apparatus 80 is configured so that in the event the sensor 72 is not triggered, as by misalignment of the cap 10 in the funnel 68, the syringe 30 will not be filled.

Figure 12:
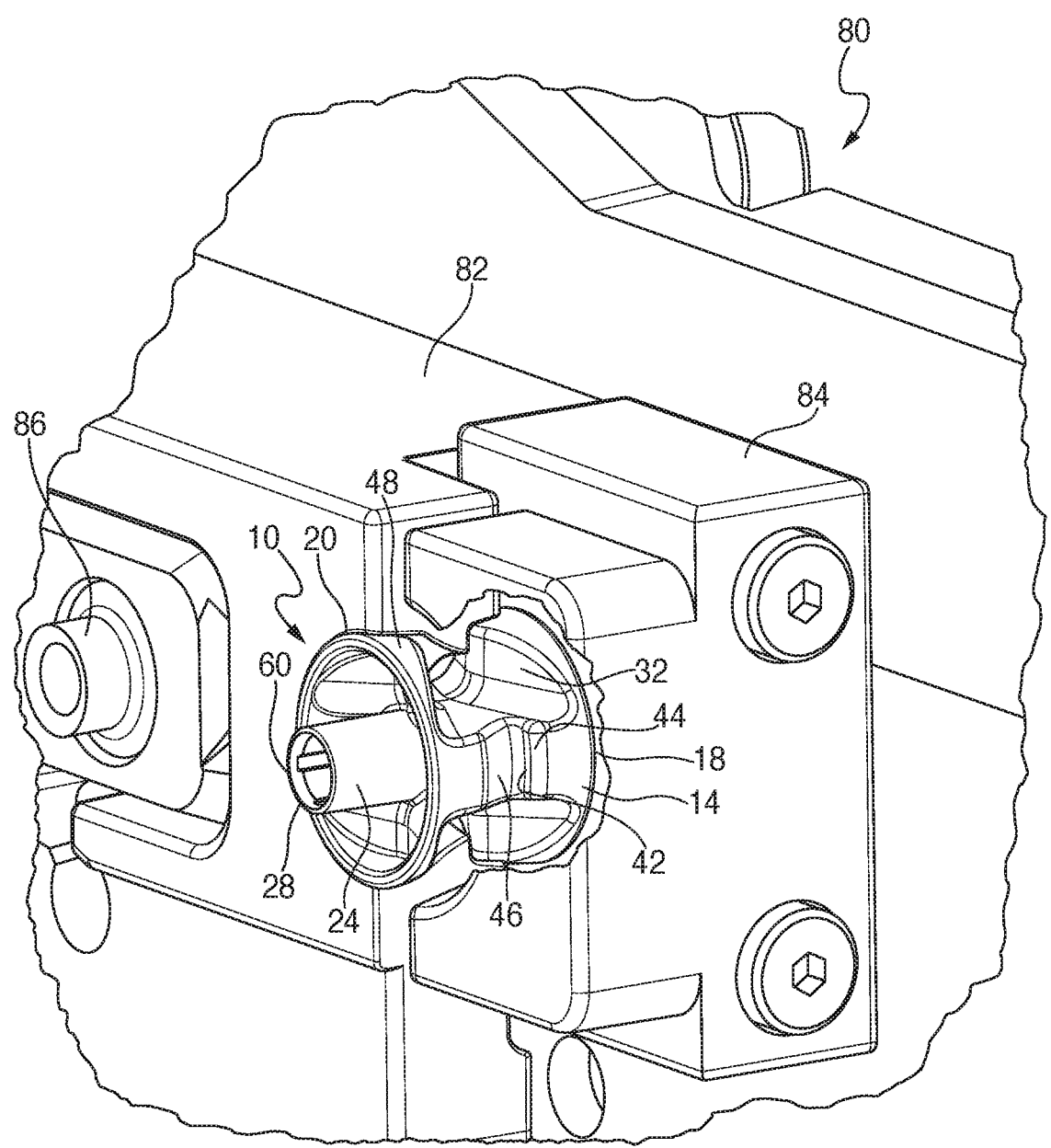
FIG. 12 is a fragmentary side perspective of a decapping/filling fixture of an automatic syringe filling apparatus shown with one of the present caps held in a decapped position.

Referring now to FIGS. 12 and 13, the syringe filling apparatus 80 includes a decapper fixture 82, which reciprocates laterally between a decapping position, illustrated, and a filling position (not shown). Once the apparatus 80 has confirmed proper positioning of the syringe 30, by activation of the sensor rod 72, the syringe is grasped by a rolling fixture portion of the apparatus and moved away from the funnel 68 so that the apparatus 80 can axially rotate and optically read markings on the syringe barrel for coordination with the system software. Next, the syringe 30 is moved by the system 80 into engagement with a decapping holder 84 that defines a cap-receiving recess that engages the undercut shoulders 42 and thus axially secures and removes the cap 10 from the syringe 30. It is preferred that the shoulders 42 are aligned with the apex 36 along the plane "A" to facilitate properly aligned engagement of the cap 10 in the holder 84. It is contemplated that the decapper fixture 82 is laterally movable relative to the holder 84 for facilitating the above-described cap engagement procedure.

The decapping fixture 82 is then reciprocated laterally by the apparatus 80 to the filling position, in which the syringe 30 is held in place, but the decapping fixture 82 moves the cap 10 out of position, and places a filling port 86 in fluid communication with the syringe outlet 61, where the syringe is filled with a designated amount of fluid. During filling, the apparatus 80 automatically retracts the syringe plunger to provide for the intake of medicinal fluid. The apparatus 80 fills the syringe 30 with the appropriate amount of fluid due to the previously-described step of optically reading the syringe barrel markings. Once filling is completed, the decapping fixture 82 reciprocates back to the position shown in FIG. 12 and the cap 10 is replaced onto the syringe outlet 61.

Referring now to FIG. 14, the syringe 30 is shown as a B-Braun PERFUSOR® syringe, and has a characteristic radially extending flange 88. A feature of the present skirt 48 is that it contacts the flange 88 once the cap 10 is installed on the syringe, facilitating location and engagement.

Referring now to FIGS. 15-20, an alternate embodiment of the cap 10 is generally designated 100, and components shared with the cap 10 are designated with identical reference numbers. A main distinguishing feature of the cap 100 is that the second or lower end 20 replaces the lower set of generally "V"-shaped ramps 32 and the apexes 36 best seen in FIG. 7, with a generally planar, radially projecting lower flange 102. The flange 102 has a first, upper surface 104 and a second, lower surface 106, as well as a diameter which generally corresponds to the diameter of the upper end 18. Thus, the flange 102 opposes the upper "V"-shaped ramp 32 and helps to define the generally hourglass shape of the cap 100.

Figure 21:
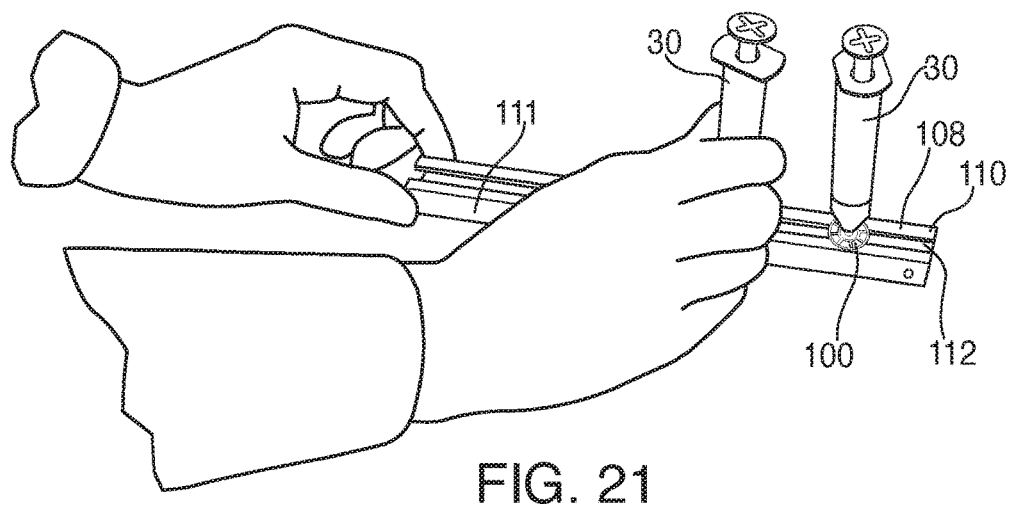
FIG. 21 is a top perspective view of a technician loading syringes equipped with the cap of FIGS. 15-19 onto a rail.

Referring now to FIGS. 21-24, the cap 100 is configured so that the first surface 104 slidingly engages an upper surface 108 of an elongate syringe storage/delivery rail 110 having a body 111 with a generally rectangular cross-section and an upper, axially extending slot 112. In addition, the rail 110 has an inner wall 114 with a second, axially extending tip slot 116 vertically displaced from the slot 112 and having a narrower lateral width. Thus, the rail 110 defines a relatively larger main chamber 118 for the cap 100, and a second, relatively smaller chamber 120 accommodating the male end or tip 26. The smaller chamber 120 is defined between the inner wall 114 and a bottom wall 122 of the rail 110. While the slots 112, 116 are dimensioned to slidably accommodate the cap 100, they cooperate with the generally planar, disk-like upper surface 104 of the flange 102 in holding the syringe 30 in the upright position as seen in FIG. 21 prior to loading into the apparatus 80.

Figure 22:
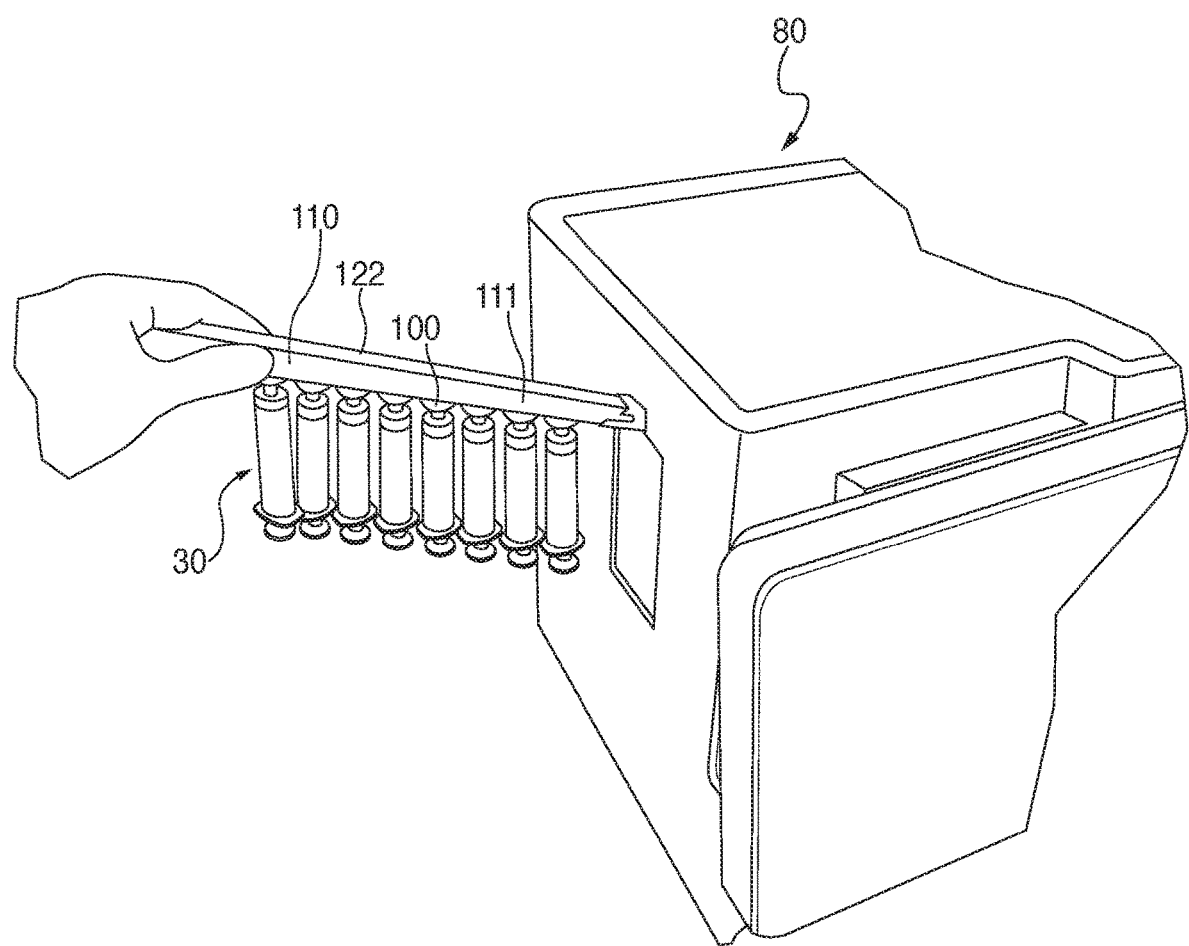
FIG. 22 is a top perspective view showing the rail of FIG. 21 inverted and syringes being loaded into an automatic filling apparatus.
Figure 23:
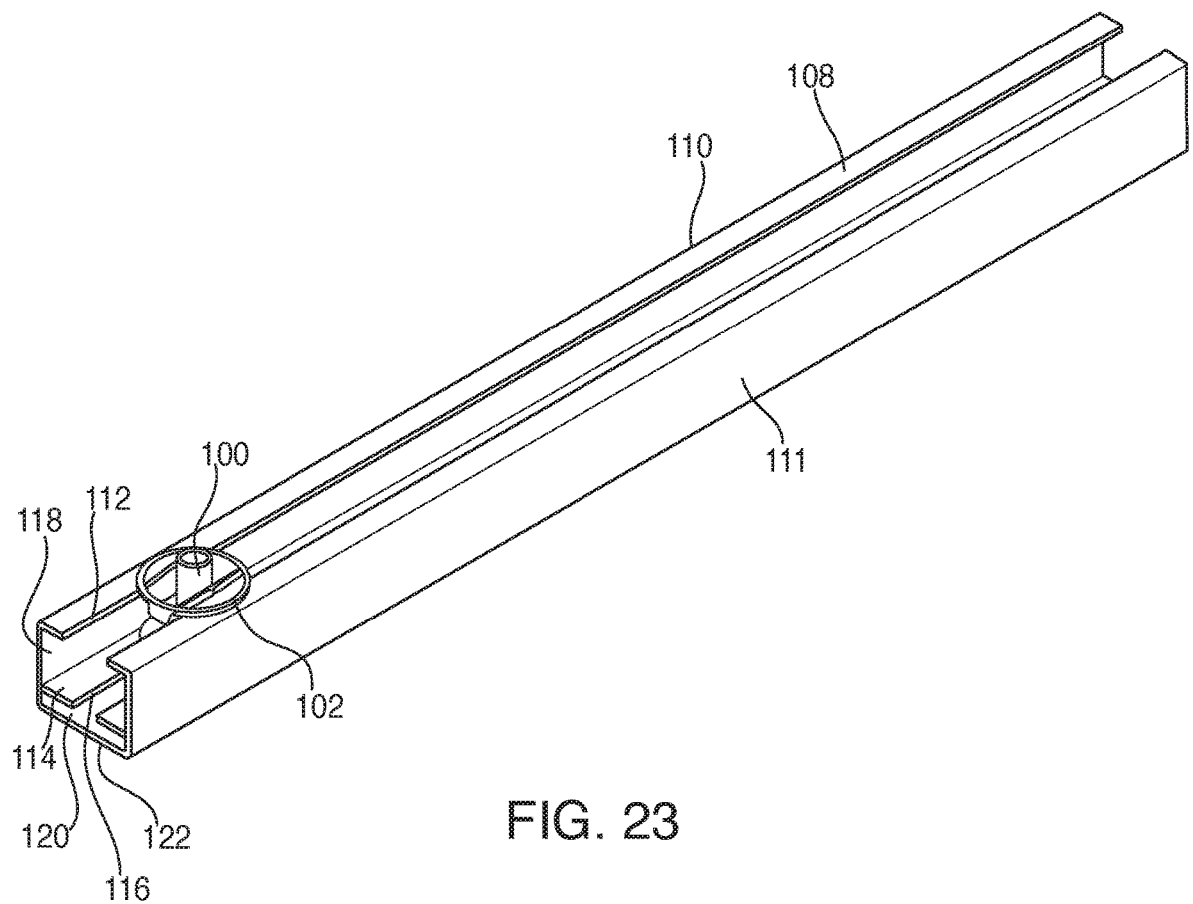
FIG. 23 is a top perspective view of the cap of FIGS. 15-19 engaged in a slot of the rail of FIG. 21.
Figure 24:
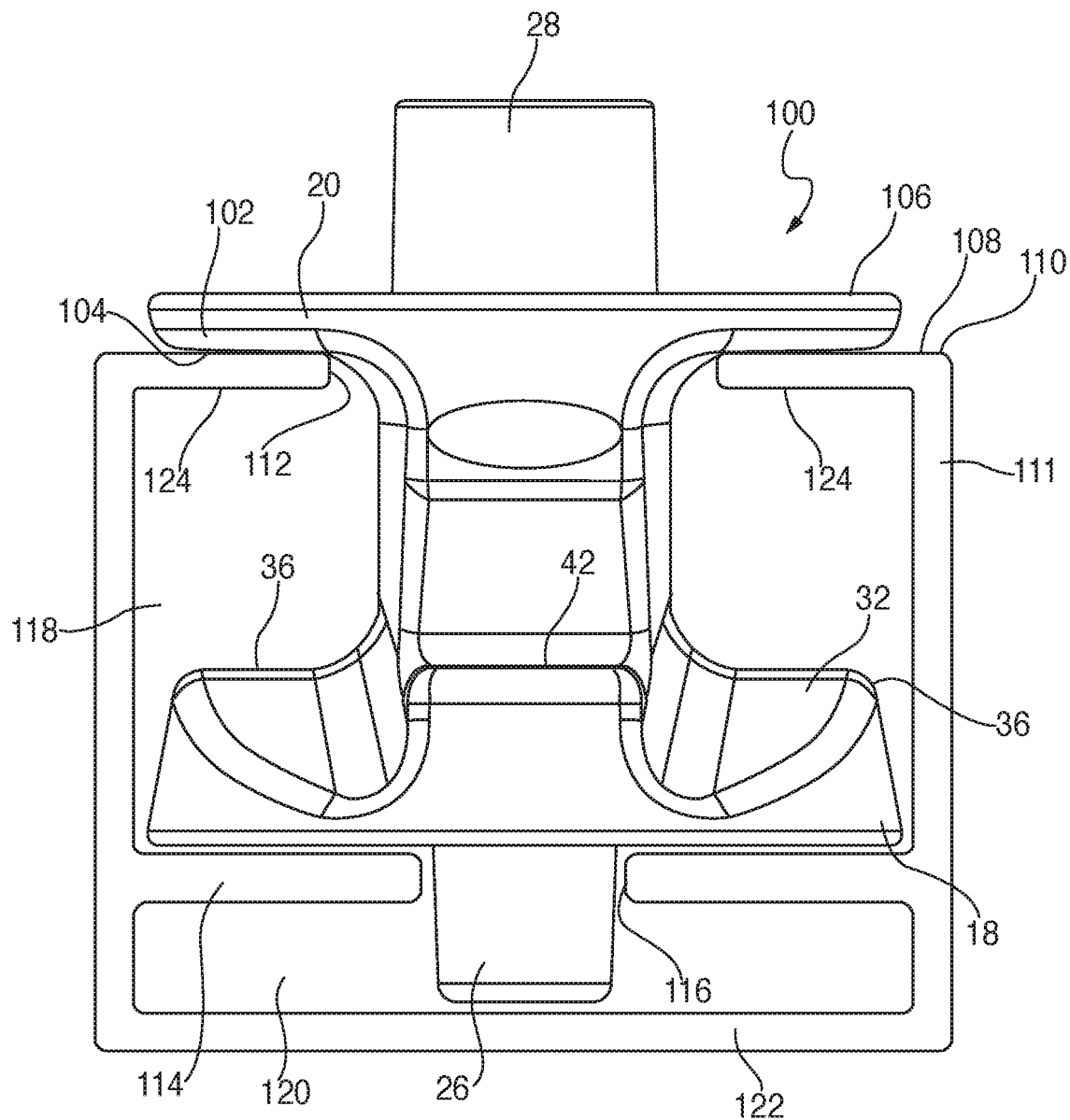
FIG. 24 is an end view of the rail of FIG. 23 with an engaged cap.

As seen in FIG. 21, the attached syringe 30 and cap 100 assemblies are slidably engaged on the rail 110 for loading purposes and are held upright as described above due to the engagement of the cap in the slot 112 and the stabilizing function of the flange 102 on the flat rail upper surface 108. Referring now to FIG. 22, once the syringes 30 are ready for insertion into the loading apparatus 80, the rail 110 and syringes are inverted and inclined so that the syringes slide by gravity towards the apparatus.

While in the loading position of FIG. 21, the cap 100 engages the upper surface 108 of the rail along the first surface 104 of the flange 102. In the inverted position, the present cap 100 slides along an inner surface 124 (FIG. 24) of the upper surface 108 of the rail 110 along the pointed apex 36 of the "V"-shaped ramps 32 having features shared with the cap 10 (FIG. 1).

Figure 25:
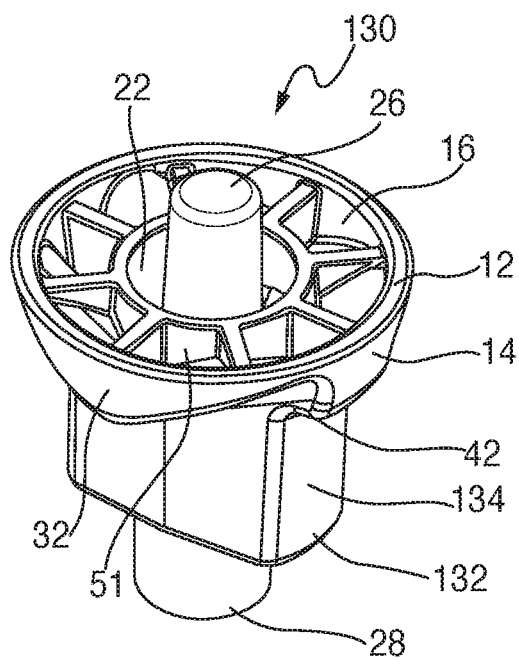
FIG. 25 is a top perspective view of another alternate embodiment of the present syringe cap.
Figure 26:
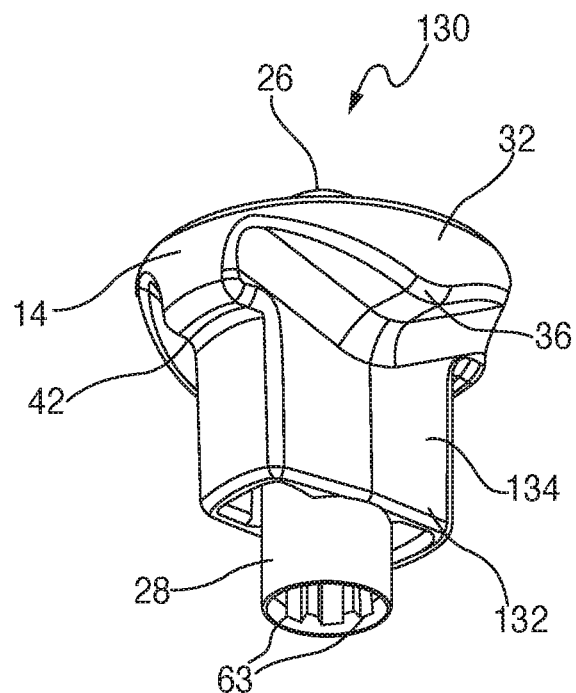
FIG. 26 is a bottom perspective view of the cap of FIG. 25.

Referring now to FIGS. 25 and 26, another alternate embodiment of the present cap is generally designated 130. Features shared with the caps 10 and 100 are identified with identical reference numbers. A main distinctive feature of the cap 130 is that the second, lower end 132, corresponding to the lower end 20, is lacking the lower V-shaped ramp 32 of the cap 10, as well as the radially projecting flange 102 of the cap 100. Instead, the cap 130 is provided with a polygonal body portion 134, which in the preferred embodiment is rectangular. However, other shapes are contemplated.

As such, the cap 130, once secured to the syringe 30 as described above in relation to the caps 10, 100, is guided on the syringe filling apparatus 30 solely by engagement of the upper "V"-shaped ramps 32. Also, the cap 130 is handled relative to the apparatus 80, and the decapper fixture 82 in the same manner as the caps 10, 100 described above.

While a particular embodiment of the present tip cap for automatic syringe filling apparatus has been shown and described, it will be appreciated by those skilled in the art that changes and modifications may be made thereto without departing from the invention in its broader aspects and as set forth in the following claims.

What is claimed:

1. A syringe cap for use with a syringe loading apparatus, said cap comprising:
    a body having an exterior surface and an interior surface, and having a first end and an opposite second end, wherein the first end includes only one "V"-shaped ramp on each of two sides of said exterior surface, wherein the second end includes only one "V"-shaped ramp on each of two sides of the exterior surface, each of the "V"-shaped ramps at the second end being opposed to one of the "V"-shaped ramps at the first end, wherein the "V"-shaped ramp on each of two sides of said exterior surface at the first end includes an apex and two terminal points, the terminal points located at a periphery of the first end and the apex located between the two terminal points and away from the periphery of the first end and towards the second end.

2. The cap of claim 1 wherein said interior surface is connected to an axially extending connector portion having a first, male end extending beyond an upper edge of said body and a second, female end extending beyond a lower edge of said body.

3. The cap of claim 2 wherein said axially extending connector portion is radially spaced from said interior surface of said body.

4. The cap of claim 2 wherein said axially extending connector portion has an interior chamber divided by a stop separating a first male portion of said chamber from a second female portion.

5. The cap of claim 4 wherein said first female portion has a diametrically flared inlet end.

6. The cap of claim 2 wherein said male end has a base provided with at least one crush rib for positively engaging a female portion of an adjacent cap when multiple caps are nested together.

7. The cap of claim 2 wherein a chamber is defined between said interior surface and said axially extending connector portion.

8. The cap of claim 7, further including a plurality of support ribs connecting said interior surface and said axially extending connector portion.

9. The cap of claim 1 wherein each "V"-shaped ramp at the second end includes an apex, such that the apexes of "V"-shaped ramps at the first end and the apexes of "V"-shaped ramps at the second end are spaced apart at a distance sufficient for slidingly accommodating rails of the apparatus.

10. The cap of claim 1 wherein said body has a pair of undercut shoulders when viewed in a second vertical cross-section taken transverse to a first vertical cross-section.

11. The cap of claim 10, wherein a generally horizontal portion of said undercut shoulders is aligned with a selected apex of a selected "V"-shaped ramp along a plane transverse to a vertical axis of said body.

12. The cap of claim 1, further comprising an axially extending connector portion having a first, male end and a second, female end, wherein at least one of the female end and the male end extend axially past respective edges of said body.

13. The cap of claim 12 wherein each of the female end and the male end extend axially past respective edges of said body approximately the same distance.

14. The cap of claim 1, further including a generally radially extending flange opposing said at least one "V"-shaped ramp on each said side of said cap.

15. A syringe tip cap for use with an automatic syringe loading apparatus, said cap comprising:
a body having an exterior surface and an interior surface, and having a first end portion and an opposite second end portion, said first end portion including only one "V"-shaped ramp on each of two outwardly facing sides of said exterior surface, wherein the "V"-shaped ramp on each of two outwardly facing sides of said exterior surface includes an apex and two terminal points, the terminal points located at a periphery of the first end portion and the apex located between the two terminal points and away from the periphery of the first end portion and towards the second end portion;
said body having a pair of undercut shoulders when viewed in a second vertical cross-section taken transverse to a first vertical cross-section; and
said interior surface being connected to an axially extending connector portion having a first, male end extending beyond an upper edge of said body and a second, female end.

16. The cap of claim 15 wherein said axially extending connector portion has an interior chamber divided by a stop separating a female portion of said chamber from a male portion, and said female portion has at least one venting channel.

17. The cap of claim 15 wherein at least one of said female end and said male ends extend axially past respective edges of said body approximately the same distance.

18. The cap of claim 15 wherein a generally horizontal portion of said undercut shoulders is aligned with a selected one of apexes of said "V"-shaped ramps along a plane transverse to a vertical axis of said body.

* * * * *